United States Patent [19]
Dröge et al.

[11] Patent Number: 6,005,129
[45] Date of Patent: Dec. 21, 1999

[54] PROCESS FOR PRODUCING THIOCYANATOPROPYLTRIETHOXYSILANE

[75] Inventors: Helmut W. Dröge, Bornheim, Germany; Hui-Li Yang, Mobile, Ala.

[73] Assignee: Degussa Corporation, Ridgefield Park, N.J.

[21] Appl. No.: 09/246,950

[22] Filed: Feb. 9, 1999

[51] Int. Cl.$^6$ .................................................. C07F 7/10
[52] U.S. Cl. ............................................................ 556/414
[58] Field of Search ............................................. 556/414

[56] References Cited

U.S. PATENT DOCUMENTS

| | | |
|---|---|---|
| 2,511,310 | 6/1950 | Upson . |
| 2,559,340 | 7/1951 | Scotia . |
| 2,762,826 | 9/1956 | Noll . |
| 3,178,391 | 4/1965 | Holtschmidt et al. . |
| 3,502,704 | 3/1970 | McKellar . |
| 3,646,089 | 2/1972 | Berger ..................................... 556/414 |
| 3,651,117 | 3/1972 | Bennett . |
| 3,759,696 | 9/1973 | Berger ..................................... 556/414 |
| 3,790,613 | 2/1974 | Berger . |
| 4,524,169 | 6/1985 | Wolff et al. . |
| 4,593,111 | 6/1986 | Crossley . |
| 4,609,748 | 9/1986 | Sheperd . |
| 5,116,886 | 5/1992 | Wolffe et al. . |
| 5,159,009 | 10/1992 | Wolff et al. . |
| 5,194,673 | 3/1993 | Wang et al. . |
| 5,219,963 | 6/1993 | Goerl et al. . |

FOREIGN PATENT DOCUMENTS

| | | |
|---|---|---|
| 280946 | 2/1987 | European Pat. Off. . |
| 126495 | 6/1959 | Russian Federation . |

OTHER PUBLICATIONS

"Cyclopentylbis 92–ethoxyethoxy) ethoxysilane and its preparation," "Cyclopentyl (2–ethoxyethoxy) dimethoxysilane and its preparation," and "Preparation of double bond-–containing organosilane compounds," *Chemical Abstracts*, vol. 123, Jun. 1995, p. 1316.

"Phenoxyisothiocyanatosilanes" and "Addition of tribenzylsilane to olenfins," *Chemical Abstracts*, 1959, p. 959 *Patent Abstracts of Japan*, vol. 011, No. 337 (P–633), Nov. 5, 1987, Publ. No.: 62–121470–A, Canon Inc, Publ. Date: Jun. 2, 1987.

Glenn D. Cooper, "Organo–silicon compounds containing the thiocyanomethyl group attached to silicon", May 7, 1954.

*Primary Examiner*—Paul F. Shaver
*Attorney, Agent, or Firm*—Smith, Gambrell & Rusell, LLP

[57] ABSTRACT

After a solution of chloropropyltriethoxysilane and sodium thiocyanate react in ethanol to form a thiocyanatopropyltriethoxysilane suspension, salt resulting from the reacting step is removed from the ethanol-containing centrifugate and washed. The first embodiment for manufacturing thiocyanatopropyltriethoxysilane includes adding the wash ethanol to the solution in the reacting step, distilling the centrifugate to remove ethanol, and removing solids from a thiocyanatopropyltriethoxysilane residue resulting from the distilling step. The ethanol from the distilling step may be used to wash the salt separated in the centrifugating step. The second embodiment in the process for manufacturing thiocyanatopropyltriethoxysilane includes distilling a thiocyanatopropyltriethoxysilane suspension to form distilled ethanol and a thiocyanatopropyltriethoxysilane residue, and centrifugating the residue to separate salt resulting from the reacting step from the centrifugate to obtain a thiocyanatopropyltriethoxysilane product. The distilled ethanol can be used to wash the salt, and the ethanol from the washing step can be added to the solution in the reacting step.

16 Claims, 12 Drawing Sheets

PROCESS FOR PRODUCING THIOCYANATOPROPYLTRIETHOXYSILANE

BACKGROUND OF THE INVENTION

This invention relates to processes for generating thiocyanatoalkyltrialkoxysilanes and preferably thiocyanatopropyltriethoxysilane.

Thiocyanatopropyltriethoxysilane is used by the rubber industry as a reinforcement agent. The EtO-groups of this silane compound show reactivity towards the OH-groups of fillers (e.g., precipitated silicas), while the SCN-group (in combination with accelerators and sulfur) reacts within the polymer. Stable bonds form, therefore, between fillers and polymer via the silane.

Thiocyanatopropyltriethoxysilane is produced by reacting chloropropyltriethoxysilane and sodium thiocyanate in ethanolic solution under elevated pressure. The typical reaction involving known reagents proceeds as follows:

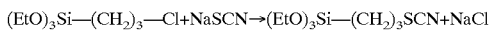

$(EtO)_3Si-(CH_2)_3-Cl+NaSCN \rightarrow (EtO)_3Si-(CH_2)_3SCN+NaCl$

Salt generated by this reaction is removed in a centrifuge immediately after the reaction. The resulting filter cake of salt is washed with ethanol and, according to the previously employed process, this wash ethanol is then mixed with the filtrate resulting from the centrifugation step. The resulting mixture is distilled and the substance is freed of the ethanol.

One of the problems with the previously employed process is the length of time it takes to distill the ethanol. Thus, it would be advantageous to the industry if the efficiency of the method could be improved by shortening the distillation time. Due to precipitation of solids previously dissolved in the ethanol as a result of the distillation step, another solid removal step must follow. Therefore, it would also be an advantage to the industry if the subsequent solid removal step could be eliminated.

SUMMARY AND OBJECTS OF THE INVENTION

One of the objects of the present invention is to provide a more efficient process for producing thiocyanatopropyltriethoxysilane.

The present invention overcomes the shortcomings of the previously employed process for producing thiocyanatopropyltriethoxysilane by a process having two embodiments. In the first embodiment, the ethanol which is used to wash the filter cake is segregated from the filtrate resulting from the centrifugation step. In contrast to the previously employed process, the filtrate portion is distilled while the ethanol used to wash the filter cake is reused in the initial reaction step according to the invention. In carrying out the process according to the invention, the first embodiment of the invention lowers the ethanol concentration in the filtrate which is subject to distillation and thus decreases the overall distillation time. In this way, the present invention enables the distillation time to be reduced virtually in half.

According to a second embodiment of the present invention, the centrifugation and distillation steps of the previously employed process are reversed. Such a reversal obviates the need for a second solid removal step, which step is necessary in the previously employed process because solids precipitate from the filtrate in the centrifugation step upon distillation. Thus, the manufacturing time is greatly reduced and process efficiency is increased.

These process steps can be applied to processes for making analogous thiocyanatoalkyltrialkoxysilanes. Starting materials are sodium thiocyanate, chloroalkylalkoxysilanes, and preferably the corresponding alcohol as a solvent. For example, chloroethyltrimethoxysilane reacts with sodium thiocyanate in methanolic solution to form thiocyanatoethyltrimethoxysilane. Although corresponding alcohols used as the solvent are preferable, other alcohols can be used, such as propanol, although lower yields or conversion rates may result.

BRIEF DESCRIPTION OF THE DRAWINGS

The present invention will be further understood with reference to the accompanying drawings, wherein.

DETAILED DESCRIPTION OF THE PREFERRED EMBODIMENTS OF THE INVENTION

Figure 5:
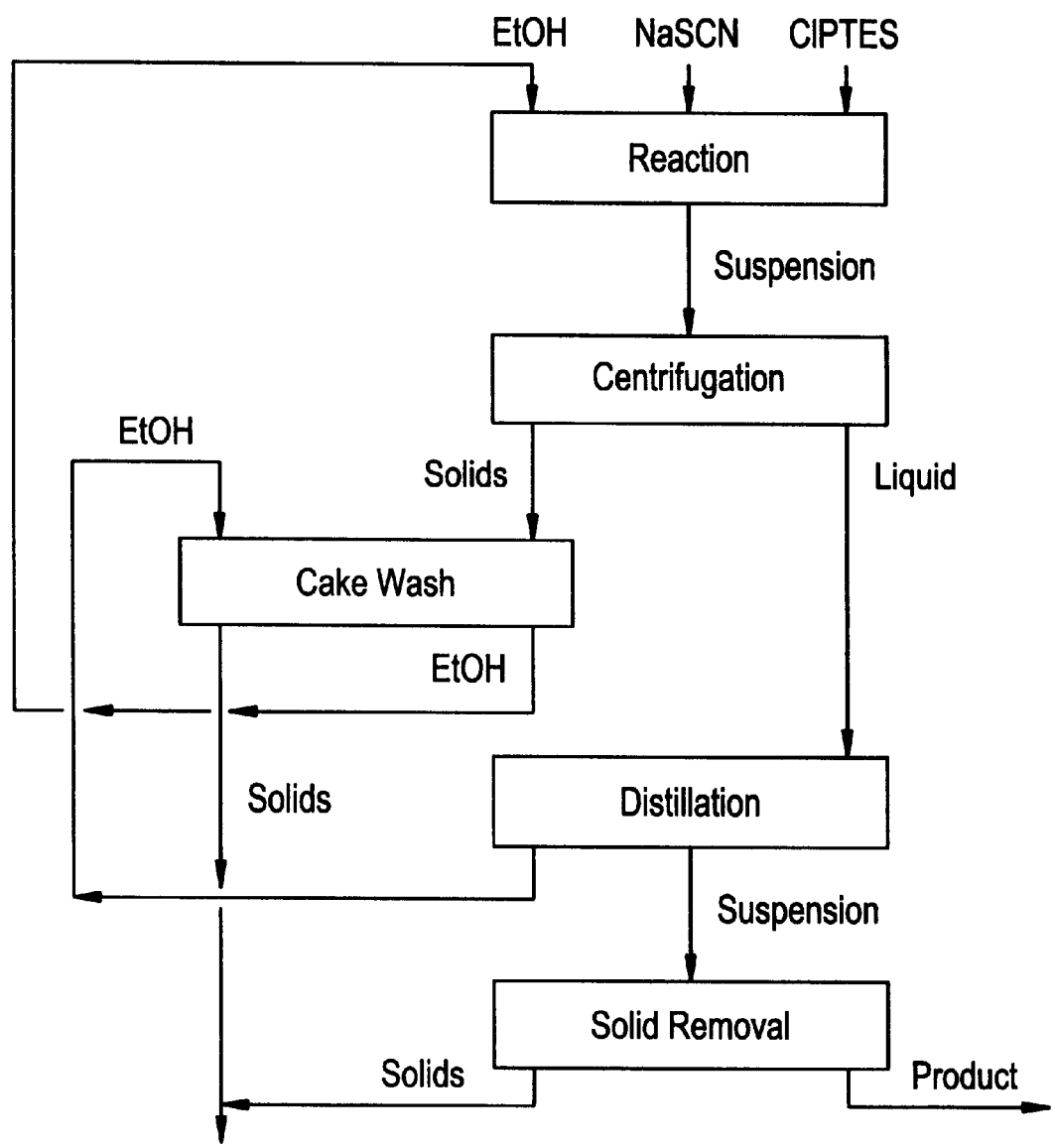
FIG. 5 is a flow diagram showing the first embodiment according to the invention, namely, the segregation of wash ethanol and filtrate from the centrifugation step.

The first embodiment of the process for manufacturing thiocyanatopropyltriethoxysilane, as illustrated in the flow diagram of FIG. 5, begins with reacting a solution of chloropropyltriethoxysilane (ClPTES) and sodium thiocyanate (NaSCN) in ethanol (EtOH) in a reaction zone to form a thiocyanatopropyltriethoxysilane suspension which is delivered from the reaction zone. A suspension refers to a mixture between a solid (salt) and a liquid (thiocyanatopropyltriethoxysilane) with or without ethanol. This reacting step is similar to the previously employed process shown in FIG. 1. The next step of the first embodiment of the invention includes centrifugating the suspension to separate salt, which results from reacting ClPTES and NaSCN and which forms a salt cake after centrifugating from the ethanol-containing suspension. Any filtration step that allows cake wash can be used instead of centrifugation such as using a filter press. The salt is separated from the thiocyanatopropyltriethoxysilane centrifugate as shown.

Figure 1:
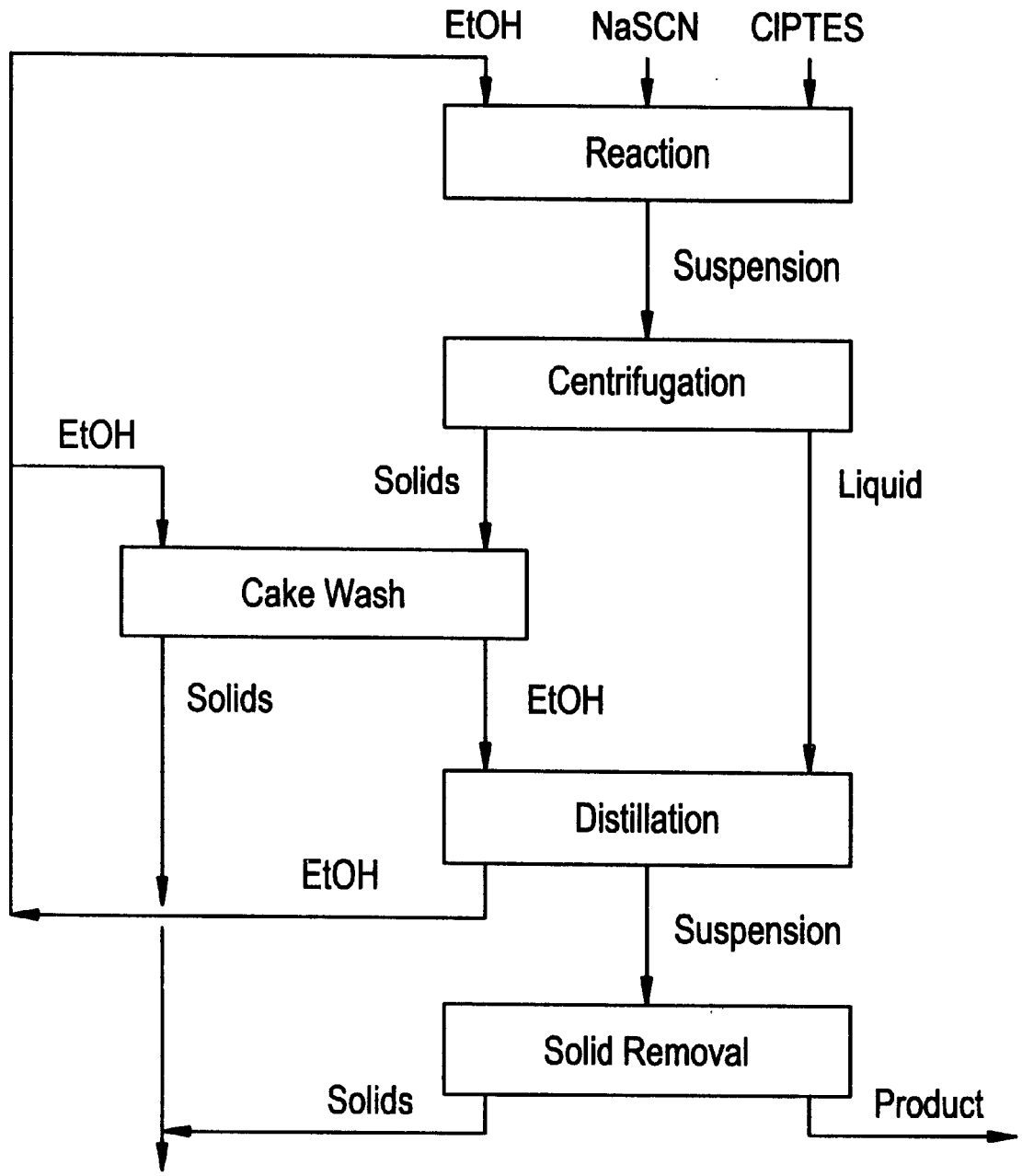
FIG. 1 shows a basic flow diagram of the previously employed process for generating thiocyanatopropyltriethoxysilane.

The next steps according to the first embodiment of the invention, include washing the salt cake with ethanol, and recirculating the ethanol from the washing step by adding the ethanol to the solution in the reacting zone. The washing and recirculating steps differ from the previously employed process shown in FIG. 1. As shown in FIG. 1, the filtrate from the centrifugation step is combined with the ethanol from the washing step. This combined liquid is then delivered to the distillation zone and distilled according to the previously employed process.

The following steps shown in FIG. 5 according to the first embodiment of the invention include distilling the centrifugate to remove ethanol and then removing solids from thiocyanatopropyltriethoxysilane residue resulting from the distilling step to form the thiocyanatopropyltriethoxysilane product. The ethanol from the distilling step can be used to wash the salt separated in the centrifugating step.

Figure 9:
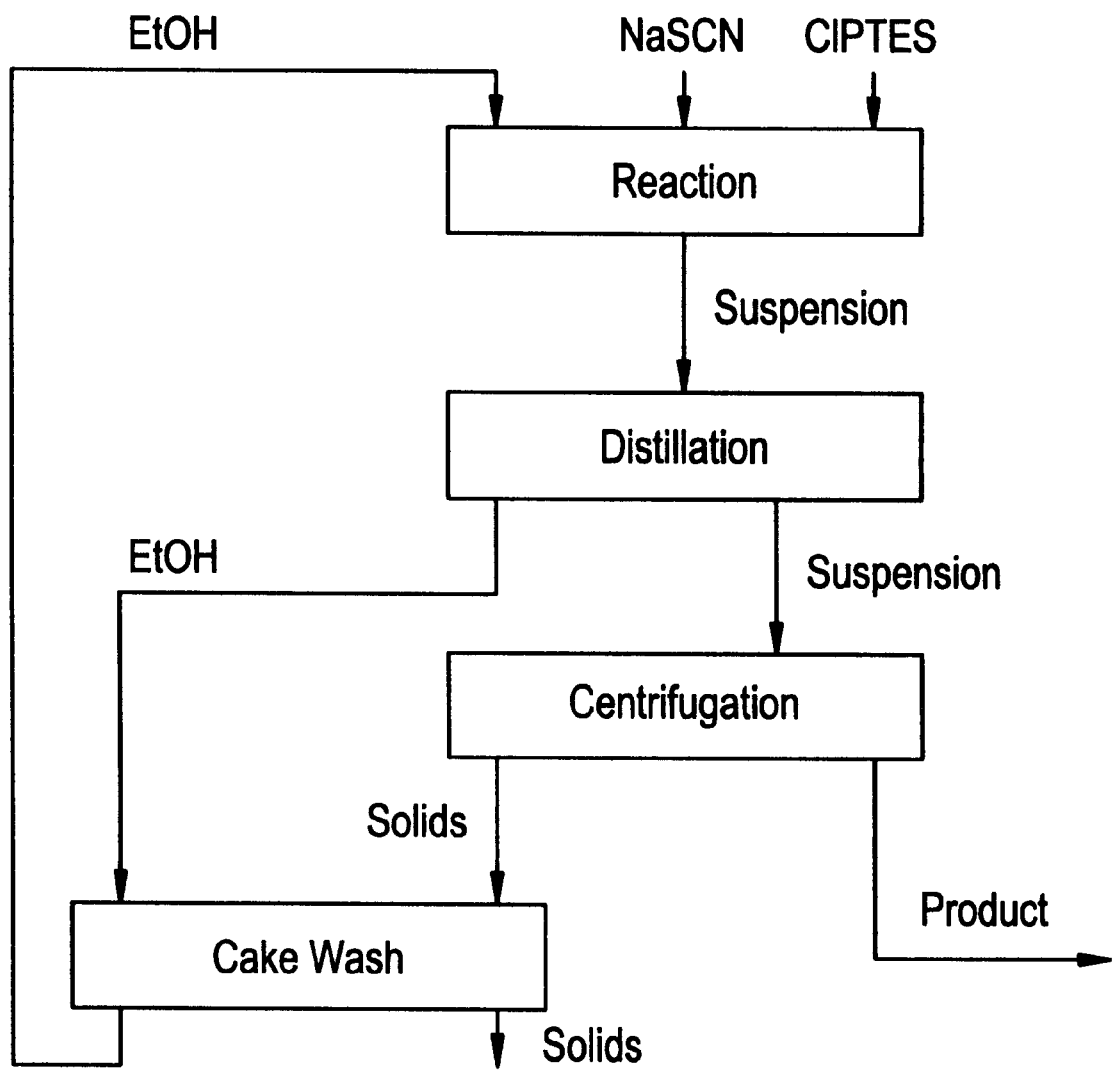
FIG. 9 is a flow diagram showing the second embodiment according to the invention, namely reversal of the centrifugation and distillation steps in relation to the previously employed process.

The second embodiment in the process for manufacturing thiocyanatopropyltriethoxysilane according to the invention is illustrated in the flow diagram of FIG. 9. This embodiment begins with reacting a solution of chloropropyltriethoxysilane and sodium thiocyanate in ethanol in a reaction zone to form a thiocyanatopropyltriethoxysilane suspension and then, distilling the suspension in the distillation zone to remove ethanol. The salt-containing thiocyanatopropyltriethoxysilane residue is transferred to the centrifugation zone and is centrifuged to separate salt, which results from reacting ClPTES and NaSCN and which forms a cake. The salt is separated from the thiocyanatopropyltriethoxysilane centrifugate product as shown in FIG. 9. The ethanol removed from the suspension in the distilling step is used to wash the salt cake as shown. The ethanol from the washing step is recirculated by adding it to the solution in the reacting step as in the first embodiment of the invention.

EXAMPLES

Summary of Results Comparing Previously Employed Process with First and Second Embodiments of the Process of the Invention Batch Times The times given are average times for the previously employed process. Estimates are given based on these times for the processes according to the first and second embodiment of the invention. The batch times for the second embodiment of the invention described below include the separation step of the first embodiment of the invention.

| Process Step | Previously Employed Process | First Embodiment of the Invention | Second Embodiment of the Invention |
| --- | --- | --- | --- |
| Reaction | 10 hours | 10 hours | 10 hours |
| Centrifugation | 8 hours | 9 hours | 9 hours |
| Distillation | 30 hours | 16 hours | 16 hours |
| Solid Removal | 4 hours | 4 hours | 0 hours |
| Total Batch Time | 52 hours (100%) | 39 hours (75%) | 35 hours (67%) |
| Batch Cycle Time | 24 hours (100%) | 20 hours (83%) | 16 hours (67%) |

Utilized Equipment

The following equipment is not needed for the second embodiment of the invention:

1 Filter Centrifuge

1 Filtrate Pump

1 Liquid Ring compressor

1 Condenser

The service and operation of the above-mentioned equipment is estimated to take about 5 to 6 operator hours per batch. Examples 1, 2 and 3 describe in detail the original process, the first embodiment of the invention, and the second embodiment of the invention, respectively, used to obtain the above results.

Energy Consumption

Substantial amounts of energy can be saved in both of the embodiments of the process of the invention compared to the original process. This savings is mainly due to evaporating smaller amounts of ethanol during distillation, bypassing several intermittent heating and cooling steps, and operating one instead of two filter centrifuges.

Product Quality

The process incorporating the second embodiment according to the invention has been simulated several times in a 500 ml stirred pressure autoclave. The obtained product quality is well within product specifications. The bis (triethoxysilylpropyl)disulfane concentration, an undesirable side product, occasionally went out of specification while employing the previously employed process (which recycles ethanol from the distillation step to the reaction solution. This side product, however, unexpectedly remained below the detection limit in all laboratory batches using the second process embodiment according to the invention. The unexpectedly advantageous results are described in detail in Example 4.

The process according to the invention can significantly reduce production costs in the manufacture of thiocyanatopropyltriethoxysilane.

Example 1

Process description of the previously employed process

FIG. 1 is a flow diagram that illustrates the previously employed process for producing thiocyanatopropyltriethoxysilane.

Figure 2:
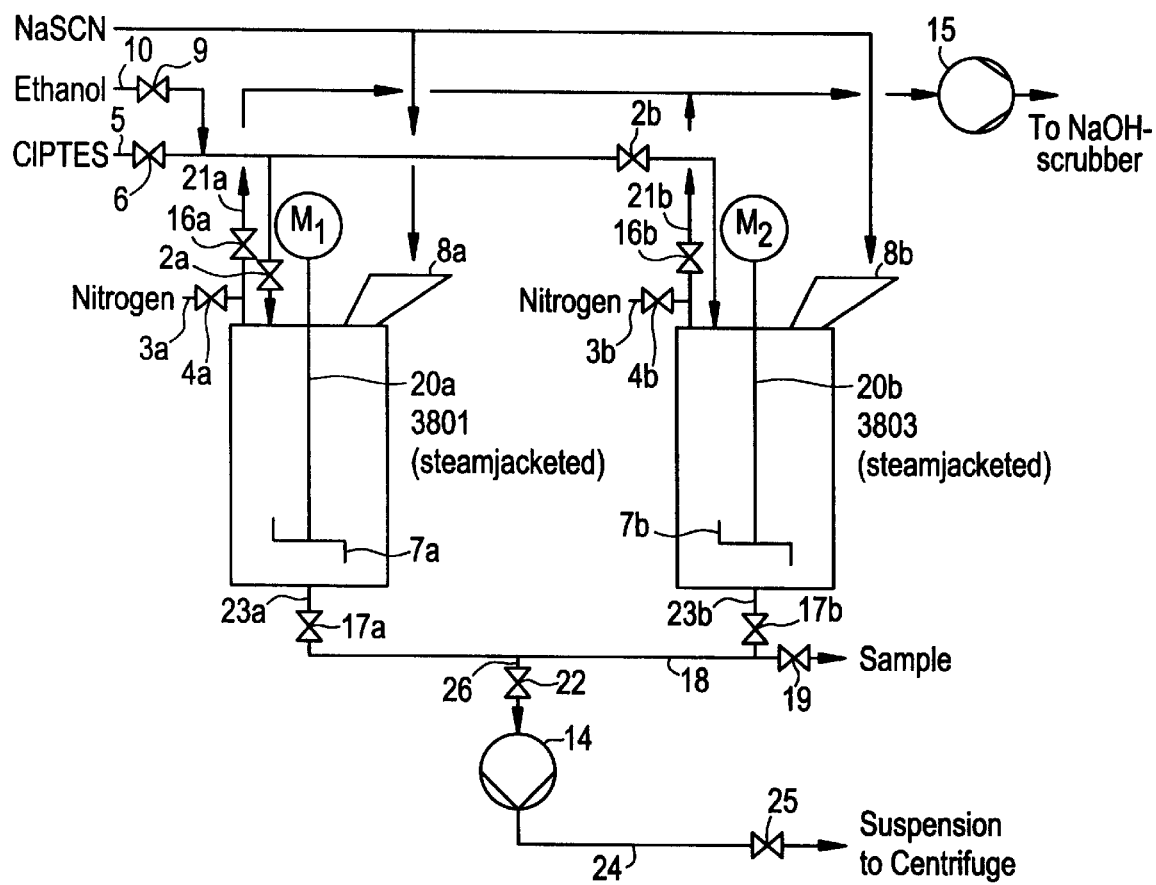
FIG. 2 is a schematic diagram detailing the reaction of chloropropyltriethoxysilane and sodium thiocyanate to produce thiocyanatopropyltriethoxysilane according to the previously employed process.

FIG. 2 is a schematic diagram corresponding to the reacting step of the previously employed process shown in the flow diagram of FIG. 1 and is described as follows. All reactions were carried out using two parallel reactors, which are 3800 l glass-lined agitated vessels 3801 and 3803. The charges and reactions in these vessels 3801 and 3803 were staged about 4 hours apart. Before each charge the atmosphere of each of the appropriate reactors was rendered inert by repeated evacuation and breaking the vacuum with nitrogen which entered the vessels 3801 and 3803 through gas lines 3a and 3b having valves 4a and 4b. Then, 1691 kg of chloropropyltriethoxysilane were introduced from feed stock line 5 having valve 6 via a flowmeter (not shown), a filter (not shown), and valves 2a and 2b respectively by means of a nitrogen pad on the chloropropyltriethoxysilane ISO container (not shown). The circulating means 20a and 20b having agitators 7a and 7b and motors $M_1$ and $M_2$ were started and 599 kg of dry NaSCN (resembling a 5 mol % excess) were then manually charged into each of the vessels 3801 and 3803 via funnels 8a and 8b, each equipped with lump catchers (not shown). After the reactor was closed, 700 kg ethanol were gravity-fed through feed stock line 10 via valve 9 which merges into feed stockline 5. Valves 2a and 2b regulate into which of the vessels 3801 and 3803 the common (merged) feedline drains.

To allow the reaction to proceed at a lower pressure, the atmosphere above the reaction mixture was partially removed by closing the vents (not shown) on vacuum lines 21a and 21b and pulling a vacuum of about 0.1 bar abs, using an ethanol ring pump 15. The gases removed by the pump 15 were sent to the NaOH scrubber (not shown). Then the vacuum lines 21a and 21b were closed at valves 16a and 16b and the contents of each of the vessels 3801 and 3803 were quickly heated to 105° C. utilizing steam on each of the vessel jackets (not shown) and resulted in a pressure increase to about 2.0–2.5 bar abs. Then the temperature was increased gradually from 105° C. to 115° C. over a six-hour period.

The reaction mixture was maintained at that temperature until a reduction of the chloropropyltriethoxysilane concentration below 2% was verified with analytical methods by analyzing samples taken from pipeline 18 through valve 19. This reaction usually took about 8 to 10 hours.

After the reaction, the suspension was cooled down to about 25° C. by running cooling water through the jackets (not shown) of the vessels 3801 and 3803. This cooling step took about 30 minutes. The resulting vacuum was then broken with nitrogen from supply lines 3a and 3b having valves 4a and 4b and the suspension was emptied out of the vessels 3801 and 3803 through a series of pipelines (pipelines 23a and 23b having valves 17a and 17b, pipeline 18, and pipeline 26 having a valve 22) by using a centrifugal pump 14. The suspension was transferred to the centrifuge 30 (shown in FIG. 3) through pipeline 24 having valve 25.

Figure 3:
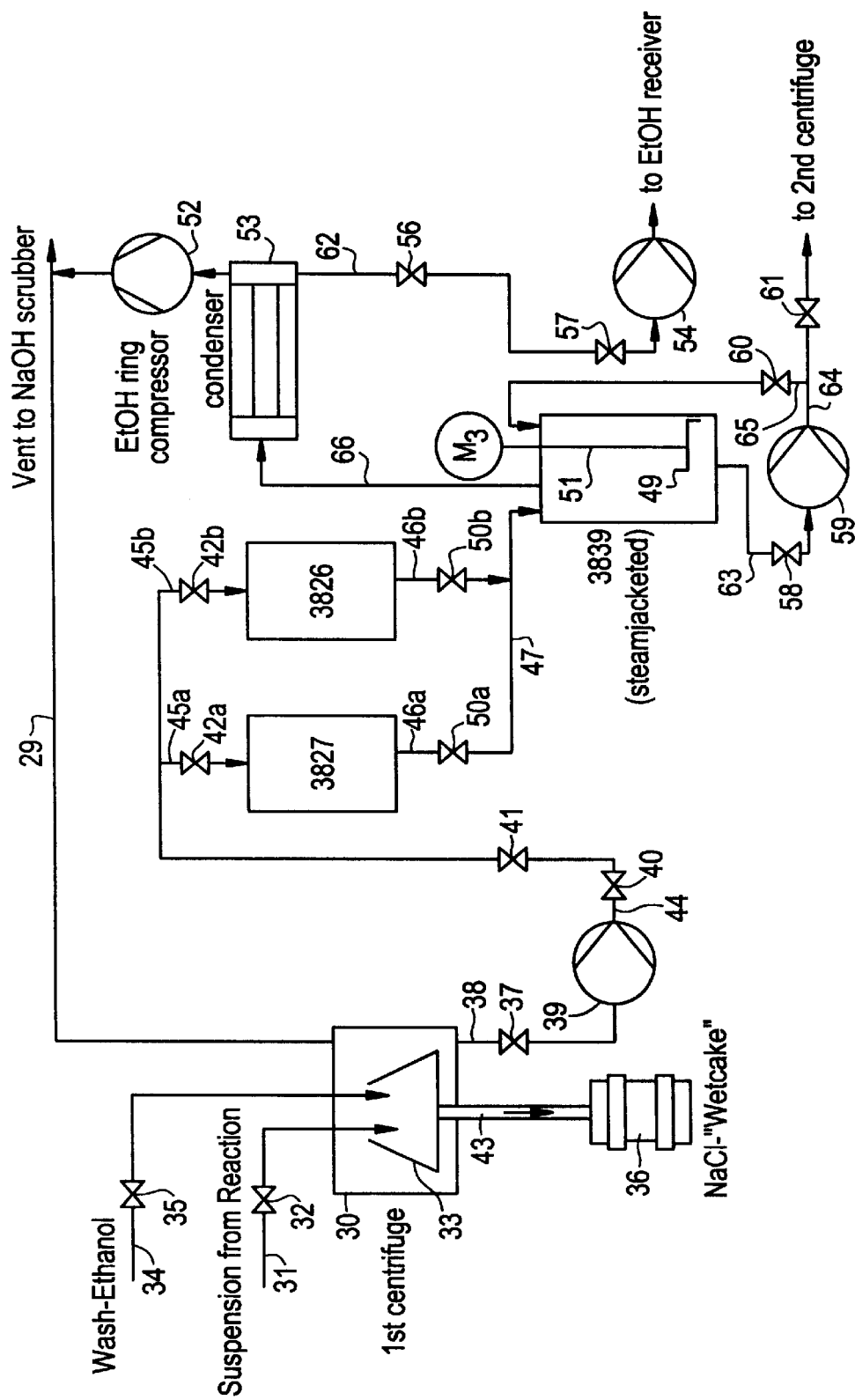
FIG. 3 is a schematic diagram of the first purification step of the previously employed process, which includes centrifugation of the suspension coming from the reactors, wash of the filter cake with ethanol, and partial removal of the product stream and ethanol by distillation.

FIG. 3 is a schematic diagram of the centrifugation and distillation steps of the previously employed process as shown in the flow diagram of FIG. 1 and is disclosed as follows. The cold suspension from the vessels 3801 and 3803 (shown in FIG. 2; was introduced into a manually operated filter centrifuge 30 through pipeline 31. The centrifugation of the suspension was attended by an operator who introduced the suspension by opening the feed valve 32 to the spinning centrifuge 30 until he could visually observe a liquid level in the centrifuge 30 through a sight glass (not shown) on top of the centrifuge 30. The feed valve 32 was then closed and the centrifuge 30 was allowed to run dry as verifiable by observation of a sight glass (not shown) in the centrifugate line 38. This step was repeated until the basket 33 in the centrifuge 30 was sufficiently filled with solids, in which case the filter cake of salt was washed with about 150 kg ethanol entering via pipeline 34 having valve 35. Any gases generated from the centrifugation were vented to an NaOH scrubber through vent line 29. After the cake was spun to dryness, it was peeled into grounded steel drums 36 via a conduit 43 using a hydraulic plow (not shown). The centrifugation of a batch (2 reactor-contents) took about 8 hours.

From here, the centrifugate which now also contained the wash ethanol was pumped through the centrifugate line 38 having a valve 37 by a pump 39, then through a pipeline 44 having valves 40 and 41, and further through pipelines 45a and 45b having valves 42a and 42b. The contents of each of the pipelines 45a and 45b were emptied into glass-lined product accumulators 3827 and 3826 respectively. From here the centrifugate was fed into the glass-lined and steam-jacketed 8000 l vessel 3839 through pipelines 46a and 46b having valves 50a and 50b and through pipeline 47. The contents, which were constantly under circulation by a circulating means 51 having an agitator 49 and a motor $M_3$, was heated up to and maintained at its boiling temperature (40° C. to 90° C.) while maintaining a vacuum of about 100 mbar abs. The vacuum was generated with an ethanol ring compressor 52.

Figure 4:
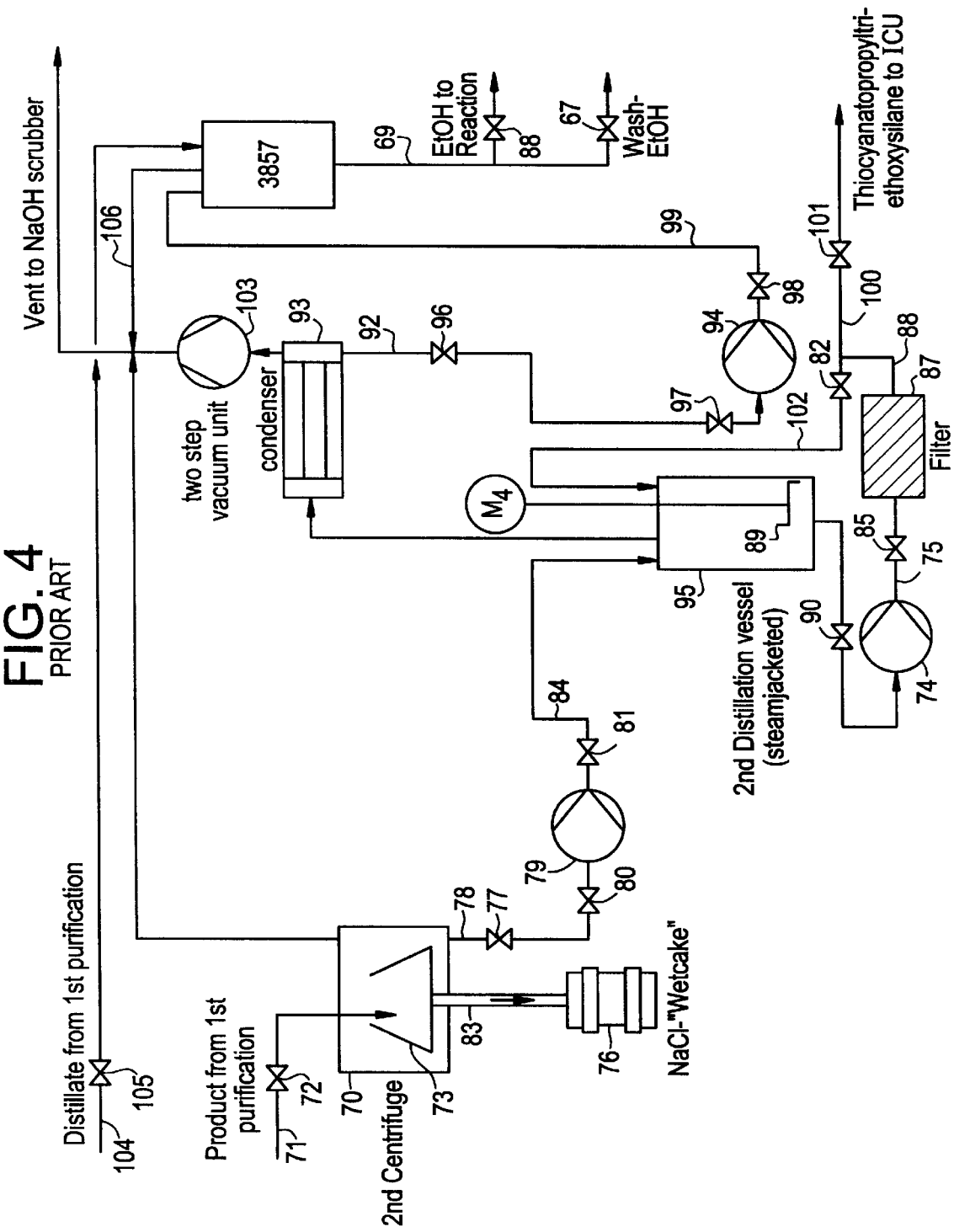
FIG. 4 is a schematic diagram of the second purification step of the previously employed process, which includes another solid removal step and final distillation of the product.

The evaporated ethanol was transferred by a conduit 66 and condensed in a chilled water-driven condenser 53 and transported through fall line 62 having valves 56 and 57 with a centrifugal pump 54 to the ethanol receiver 3857 via line 104, having valve 105 (shown in FIG. 4). The obstruction of line 63 with solids precipitated during the distillation was deterred by circulating the contents of vessel 3839 through line 63, having valve 58, pump 59, line 64, and line 65 having valve 60. During the distillation, pump 59 is running, valve 61 is closed, and valves 58 and 60 are open. This distillation step was very time-consuming and took about 24 hours. After the flow of distillate had stopped, which could be observed through a sight glass (not shown) in the fall line 62 from the condenser 53, the steam to the jacket (not shown) of the vessel 3839 was closed and the vacuum was broken with nitrogen.

The distillation residue from the vessel 3839 from which the ethanol was removed was pumped through pipelines 63 and 64 having valves 58 and 61 by a circulation pump 59 to the second centrifuge 70 (shown in FIG. 4).

FIG. 4 is a schematic diagram of the solids removal steps illustrated in the flow diagram of FIG. 1 used in the previously employed process, which diagram is described as follows. The thiocyanatopropyltriethoxysilane-containing contents were cooled to below 40° C. and transferred into the second centrifuge 70 through pipeline 71 having valve 72, utilizing pump 64 (shown in FIG. 3). This second centrifuge removed solids which precipitated during the evaporation of ethanol in the previous step. Valve 72 was then closed and the second centrifuge 70 was allowed to run dry as verified by observing a sight glass (not shown) in the filtrate line. The step was repeated until the basket 73 contained solids. The operation of this centrifuge was basically identical to the first one; however, centrifugation was faster (about 4 hours). No wash-EtOH was used to recover product from the cake of the second centrifuge. After the cake was spun to dryness, it was peeled into grounded steel drums 76 via a conduit 83, using a hydraulic plow (not shown).

The clear effluent of the second centrifuge was transferred through pipeline 78 having valves 77 and 80 and transported using a pump 79 through a pipeline 84 having a valve 81 to a second glass-lined and steam-jacketed distillation vessel 95 with a capacity of 8000 l. The contents of the second vessel 95 were circulated by a circulation means 91 having an agitator 89 and a motor $M_4$. In contrast to the first distillation, the material was constantly circulated back to the vessel 95 through a pipeline 86 having a valve 90 using a pump 74, and then through pipeline 75 having a valve 85 to a filter 87 and then through pipeline 88 which connects to pipeline 102 having a valve 82. The temperature in the vessel 95 was maintained at 90° C., while a vacuum of about 25 mbar abs, generated by a 2-stage vacuum unit (roots blower) 103, was applied. The gases resulting from the vacuum unit 103 were vented to a NaOH scrubber (not shown). Very similar to the first distillation, vapors were condensed in a chilled water cooled condenser 93 and transported via pipeline 92 having valves 96 and 97 by a pump 94 and then through pipeline 99 having a valve 98 into the ethanol receiver 3857, from where the ethanol for reaction and the ethanol for wash originate and which feed through branched pipe 69 through valves 68 and 67. This step took about 4 to 6 hours. Ethanol receiver 3857 was vented to the NaOH scrubber (not shown) through conduit 106. As soon as an ethanol concentration of less that 0.25% was analytically verified, the contents of the vessel 95 were cooled down and were loaded into bulk drums (not shown) via filter 87 and via pipeline 88 which connects to pipeline 100 having valve 101.

Example 2

Process description of first embodiment of process (washing salt cake with distilled ethanol and adding resulting ethanol to reaction mixture)

FIG. 5 is a flow diagram that illustrates the first embodiment of the process for producing thiocyanatopropyltriethoxysilane according to the invention.

Figure 6:
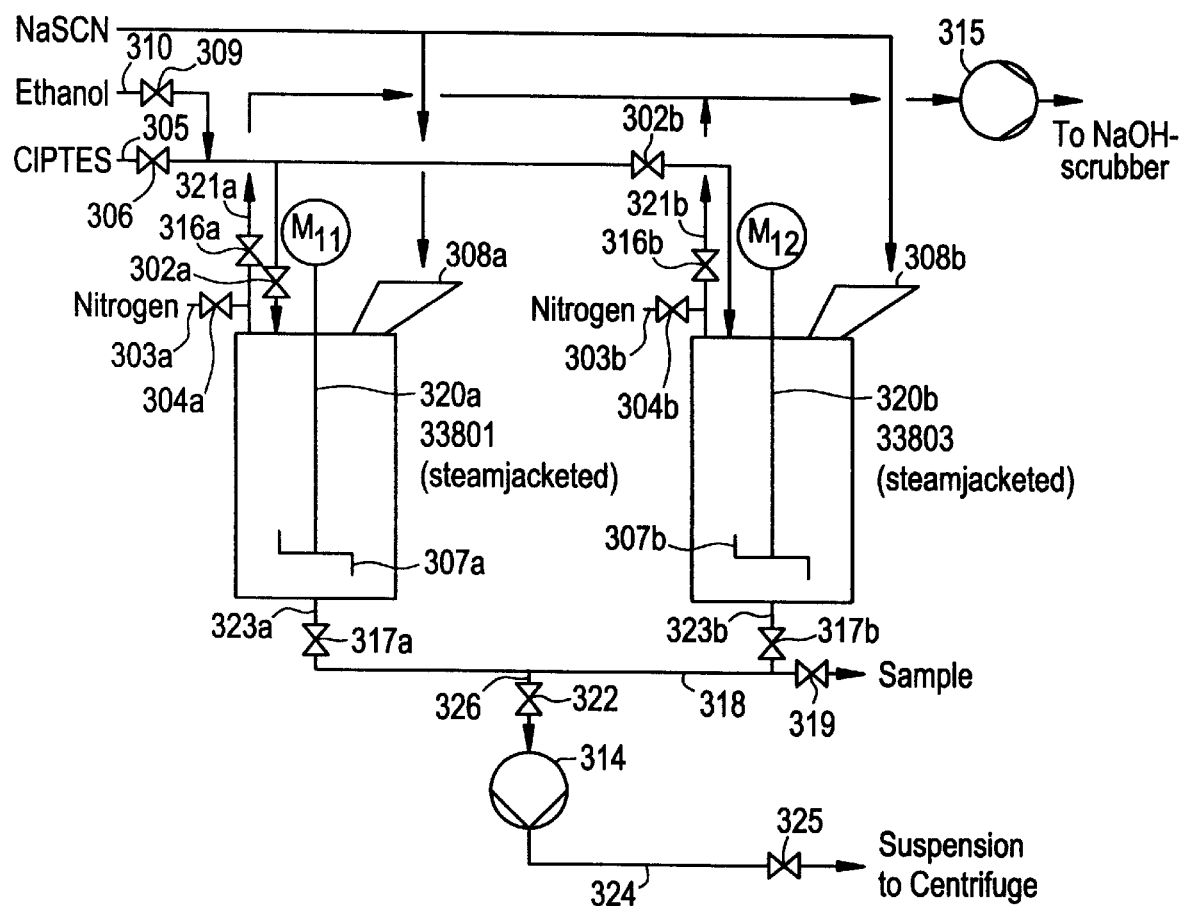
FIG. 6 is a schematic diagram detailing the reaction of chloropropyltriethoxysilane and sodium thiocyanate to produce thiocyanatopropyltriethoxysilane according to the first embodiment of the invention (which reaction step is nearly identical to the previously employed process except that the ethanol used in the reaction is not sourced from the distillate vessel)

FIG. 6 is a schematic diagram corresponding to the reacting step of the first embodiment of the process of the invention shown in the flow diagram of FIG. 5 and is described as follows. All reactions are carried out using two parallel reactors, which are 3800 l glass-lined agitated vessels 33801 and 33803. The charges and reactions in these vessels 33801 and 33803 are staged about 4 hours apart. Before each charge, the atmosphere of each of the appropriate reactors is rendered inert by repeated evacuation and breaking the vacuum with nitrogen which enters the vessels 33801 and 33803 through gas lines 303a and 303b having valves 304a and 304b. Then, 1691 kg of chloropropyltriethoxysilane are introduced from feed stock line 305 having valve 306 via a flowmeter (not shown), a filter (not shown), and valves 302a and 302b, respectively, by means of a nitrogen pad on the chloropropyltriethoxysilane ISO container (not shown). The circulating means 320a and 320b having agitators 307a and 307b and motors $M_{11}$ and $M_{12}$ are started and 599 kg of dry NaSCN (resembling a 5 mol % excess) are then manually charged into each of the vessels 33801 and 33803 via funnels 308a and 308b, each equipped with lump catchers (not shown). After the reactor is closed, 700 kg ethanol from vessel 408 (shown in FIG. 7) are gravity-fed through feed stock line 310 via valve 309 which merges into feed stockline 305. Valves 302a and 302b regulate which of the vessels 33801 and 33803 the common (merged feedline drains.

To allow the reaction to proceed at a lower pressure, the atmosphere above the reaction mixture is partially removed by closing the vents (not shown) on vacuum lines 321a and 321b and pulling a vacuum of about 0.1 bar abs, using an ethanol ring pump 315. The gases removed by the pump 315 are sent to the NaOH scrubber (not shown). Then the vacuum lines 321a and 321b are closed at valves 316a and 316b and the contents of each of the vessels 33801 and 33803 are quickly heated to 105° C. utilizing steam on each of the vessel jackets (not shown) and resulted in a pressure increase to about 2.0–2.5 bar abs. Then the temperature is increased gradually from 105° C. to 115° C. over a six-hour period.

The reaction mixture is maintained at that temperature until a reduction of the chloropropyltriethoxysilane concentration below 2% is verified with analytical methods by analyzing samples taken from pipeline 318 through valve 319. This reaction usually takes about 8 to 10 hours.

After the reaction, the suspension is cooled down to about 25° C. by running cooling water through the jackets (not shown) of the vessels 33801 and 33803. This cooling step takes about 30 minutes. The resulting vacuum is then broken with nitrogen from supply lines 303a and 303b having valves 304a and 304b and the suspension is emptied out of the vessels 33801 and 33803 through a series of pipelines (pipelines 323a and 323b having valves 317a and 317b, pipeline 318, and pipeline 326 having a valve 322) by using a centrifugal pump 314. The suspension is transferred to the centrifuge 330 (shown in FIG. 7) through pipeline 324 having valve 325.

Figure 7:
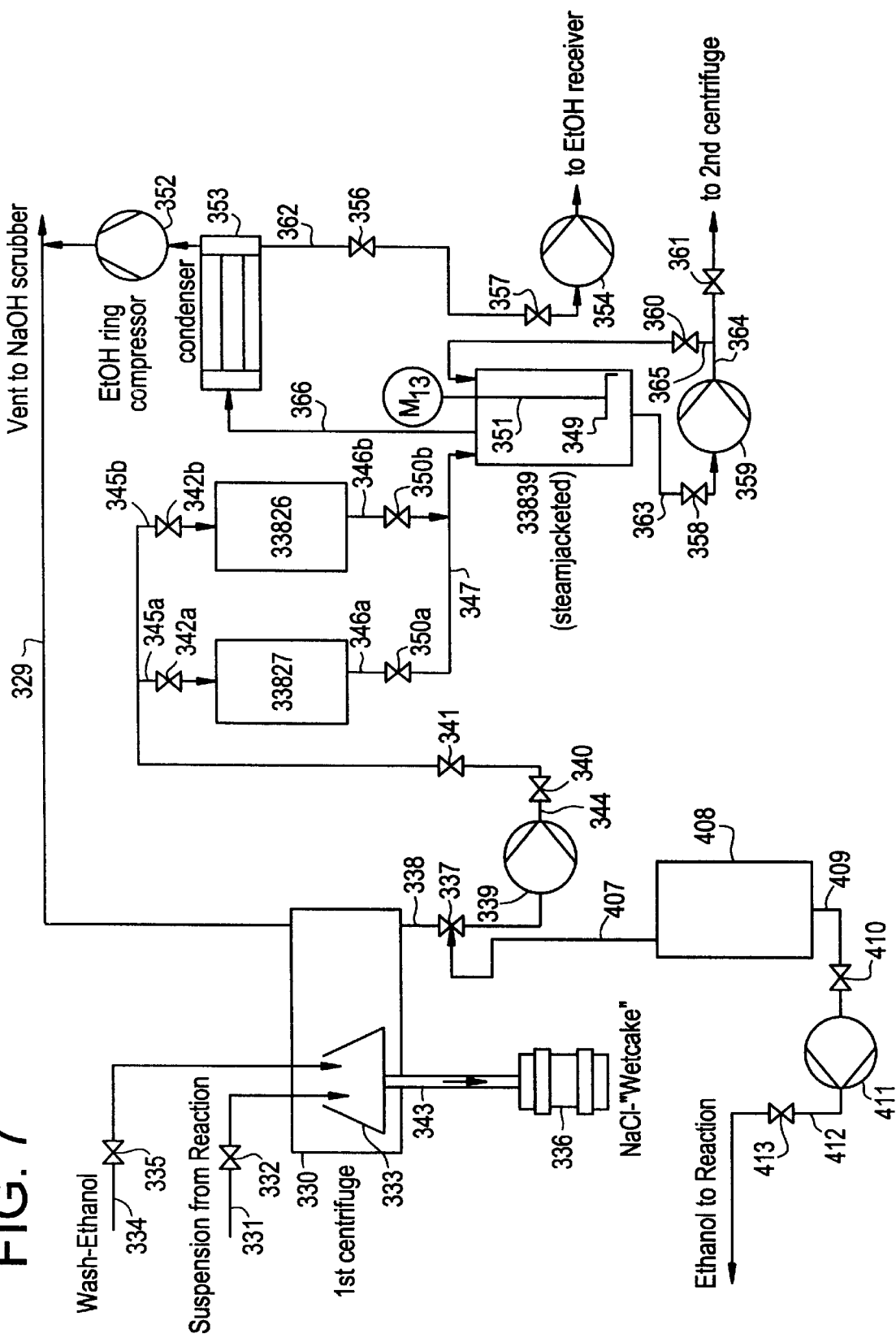
FIG. 7 is a schematic diagram of the first embodiment of the invention wherein the filtrate ethanol from the first purification step and the wash ethanol are separated.

FIG. 7 is a schematic diagram of the centrifugation and distillation steps of the previously employed process as shown in the flow diagram of FIG. 5 and is disclosed as follows. The cold suspension from the vessels 33801 and 33803 (shown in FIG. 6) is introduced into a manually operated filter centrifuge 330 through pipeline 331. The centrifugation of the suspension is attended by an operator who introduced the suspension by opening the feed valve 332 to the spinning centrifuge 330 until he could visually observe a liquid level in the centrifuge 330 through a sight glass (not shown) on top of the centrifuge 330. The feed valve 332 is then closed and the centrifuge 330 is allowed to run dry as verifiable by observation of a sight glass (not shown) in the centrifugate line 338. This step is repeated until the basket 333 in the centrifuge 330 is sufficiently filled with solids.

Before a wash cycle, the centrifuge is allowed to spin dry and the three-way valve 337 is switched. The filter cake of salt is washed with about 150 kg ethanol entering via pipeline 334 having valve 335. The ethanol that is used to wash the filter cake is separated from the centrifugate and is directed through three-way valve 337 or through pipeline 407 to vessel 408. This ethanol used to wash the filter cake supplies ethanol used in the reaction step through pipeline 409 having valve 410, which is transferred to the reaction zone using pump 411 through pipeline 412 and valve 413. This step differs from the previously employed process in that the centrifugate and the ethanol used to wash the filter cake are segregated. Such segregation allows the centrifugate to be distilled in order to remove ethanol in less time than if the combined centrifugate and ethanol used to wash the filter cake were both distilled to remove ethanol as in the previously employed process.

Any gases generated from the centrifugation are vented to an NaOH scrubber (not shown) through vent line 329. After the cake is spun to dryness, it is peeled into grounded steel drums 336 via a conduit 343 using a hydraulic plow (not shown). The centrifugation of a batch (2 reactor-contents) takes slightly longer than the previously employed process due to operating the valves that segregate the centrifugate from the ethanol used to wash the filter cake.

From here, the centrifugate is pumped through the centrifugate line 338 having a three-way valve 337 by a pump 339, then through a pipeline 344 having valves 340 and 341, and further through pipelines 345a and 345b having valves 342a and 342b. The contents of each of the pipelines 345a and 345b are emptied into glass-lined product accumulators 33827 and 33826 respectively. From here the centrifugate is fed into the glass-lined and steam-jacketed 8000 l vessel 33839 through pipelines 346a and 346b having valves 350a and 350b and through pipeline 347. The contents, which are constantly under circulation by a circulating means 351 having an agitator 349 and a motor $M_{13}$, is heated up to and maintained at its boiling temperature (40° C. to 90° C.) while maintaining a vacuum of about 100 mbar abs. The vacuum is generated with an ethanol ring compressor 352.

Figure 8:
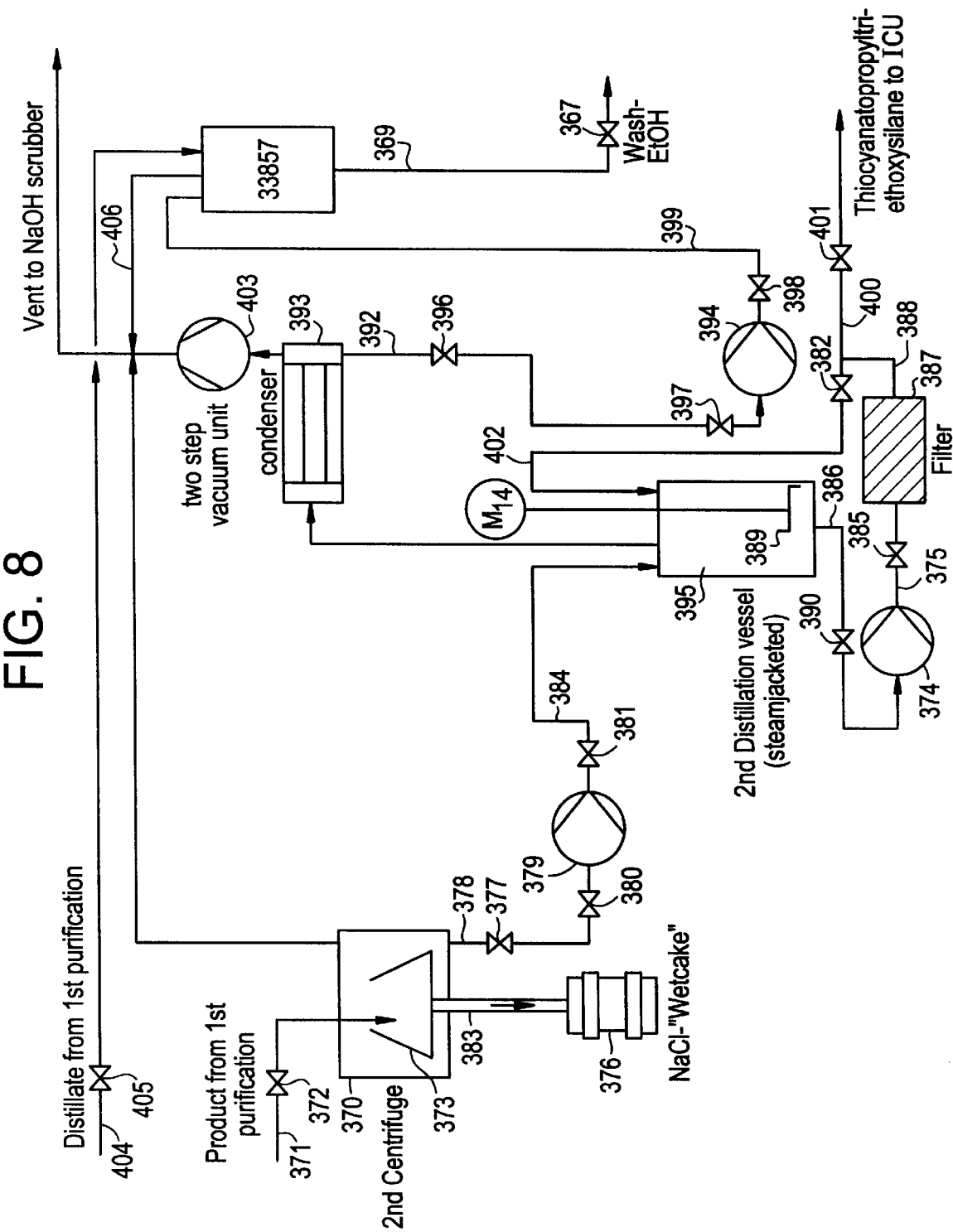
FIG. 8 is a schematic diagram of the first embodiment of the invention wherein the second purification step includes using the distillate as wash ethanol only.

The evaporated ethanol is transferred by a conduit 366 and condensed in a chilled water-driven condenser 353 and transported through fall line 362 having valves 356 and 357 with a centrifugal pump 354 to the ethanol receiver 33857 via line 404, having valve 405 (shown in FIG. 8). The obstruction of line 363 with solids precipitated during the distillation is deterred by circulating the contents of vessel 33839 through line 363, having valve 358, pump 359, line 364, and line 365 having valve 360. During the distillation, pump 359 is running, valve 361 is closed, and valves 358 and 360 are open. This distillation step takes significantly less time than the previously employed process due to the lower amount of ethanol to be evaporated. After the flow of distillate is stopped, which can be observed through a sight glass (not shown) in the fall line 362 from the condenser 353, the steam to the jacket (not shown) of the vessel 33839 is closed and the vacuum is broken with nitrogen.

The distillation residue from the vessel 33839 from which the ethanol is removed is pumped through pipelines 363 and 364 having valves 358 and 361 by a circulation pump 359 to the second centrifuge 370 (shown in FIG. 8).

FIG. 8 is a schematic diagram of the solids removal steps illustrated in the flow diagram of FIG. 5 used in the first embodiment of the process, which diagram is described as follows. The thiocyanatopropyltriethoxysilane-containing contents are cooled to below 40° C. and transferred into the second centrifuge 370 through pipeline 371 having valve 372, utilizing a pump 364 (shown in FIG. 7). This second centrifuge removes solids which precipitated during the evaporation of ethanol in the previous step. Valve 372 is then closed and the second centrifuge 370 is allowed to run dry as verified by observing a sight glass (not shown) in the filtrate line. The step is repeated until the basket 373 contained solids. The operation of this centrifuge was basically identical to the first one; however, centrifugation is faster (about 4 hours). No wash-EtOH is used to recover product from the cake of the second centrifuge. After the cake is spun to dryness, it is peeled into grounded steel drums 376 via a conduit 383, using a hydraulic plow (not shown).

The clear effluent of the second centrifuge is transferred through pipeline 378 having valves 377 and 380 and pumped using a pump 379 through a pipeline 384 having a valve 381 to a second glass-lined and steam-jacketed distillation vessel 395 with a capacity of 8000 l. The contents of the second vessel 395 is circulated by a circulation means 391 having an agitator 389 and a motor $M_{14}$. In contrast to the first distillation, the material is constantly circulated back to the vessel 395 through a pipeline 386 having a valve 390 using a pump 374, and then through pipeline 375 having a valve 385 to a filter 387 and then through pipeline 388 which connects to pipeline 402 having a valve 382. The temperature in the vessel 395 is maintained at 90° C., while a vacuum of about 25 mbar abs, generated by a 2-stage vacuum unit (roots blower) 403, is applied. The gases resulting from the vacuum unit 403 are vented to a NaOH scrubber (not shown). Very similar to the first distillation, vapors are condensed in a chilled water cooled condenser 393 and transported via pipeline 392 having valves 396 and 397 by a pump 394 and then through pipeline 399 having a valve 398 into the ethanol receiver 33857, from where the ethanol for wash originate and which feed through branched pipe 369 through valve 367. This step takes about 4 to 6 hours. Ethanol receiver 33857 is vented to the NaOH scrubber (not shown) through conduit 406. As soon as an ethanol concentration of less that 0.25% is analytically verified, the contents of the vessel 395 are cooled down and are loaded into bulk drums (not shown) via filter 387 and via pipeline 388 which connects to pipeline 400 having valve 401.

Example 3

Process description of second embodiment of process (reversal of centrifugation and distillation steps)

Figure 10:
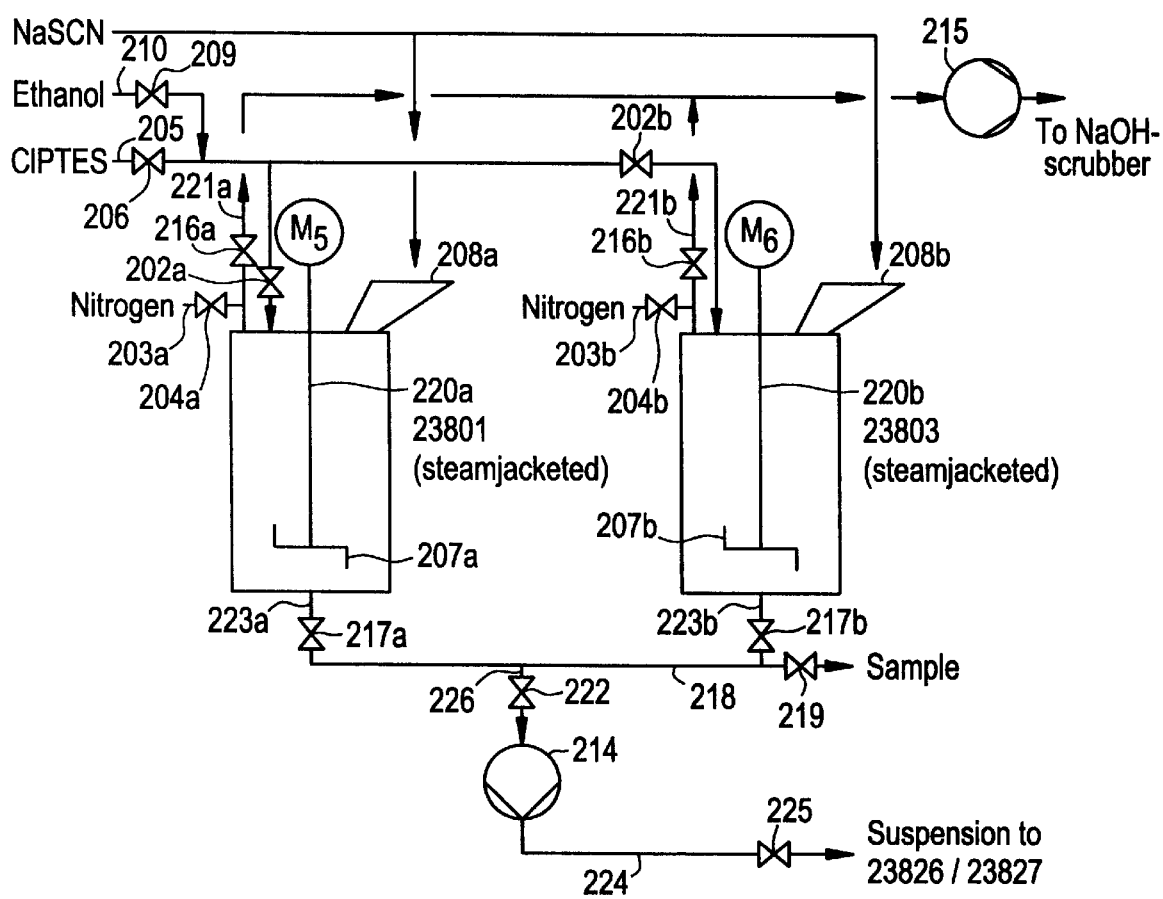
FIG. 10 is a schematic diagram detailing the reaction of chloropropyltriethoxysilane and sodium thiocyanate to produce thiocyanatopropyltriethoxysilane according to the second embodiment of the invention (which reaction step is nearly identical to the previously employed process)

The reactions are carried out in the same reactors described in Example 1 and are shown in FIG. 10, using identical equipment, operating conditions, and amounts of raw materials. The process of the second embodiment can be combined with process steps of the first embodiment in which case solvent ethanol does not come from a common ethanol receiver as in Example 1 but from a vessel which collects wash ethanol as described in this example.

FIG. 10 is a schematic diagram corresponding to the reacting step shown in the flow diagram of FIG. 9 and is described as follows. All reactions are carried out using two parallel 3800 l glass-lined agitated vessels 23801 and 23803. The charges and reactions in these vessels 23801 and 23803 are staged about 4 hours apart. Before each charge each of the appropriate reactors is rendered inert by repeated evacuation and breaking the vacuum with nitrogen which enters the vessels 23801 and 23803 through gas lines 203*a* and 203*b* having valves 204*a* and 204*b*. Then, 1691 kg of chloropropyltriethoxysilane are introduced from feed stock line 205 having a valve 206 via a flowmeter (not shown), a filter (not shown), and valves 202*a* and 202*b* respectively by means of a nitrogen pad (not shown) on the chloropropyltriethoxysilane ISO container (not shown). The circulating means 220*a* and 220*b* having agitators 207*a* and 207*b* and motors $M_5$ and $M_6$ are started and 599 kg of dry NaSCN (resembling a 5 mol % excess) are then manually charged into each of the vessels 23801 and 23803 via funnels 208*a* and 208*b*, each equipped with lump catchers (not shown). After the reactor is closed, 700 kg ethanol are gravity-fed via valve 209 through feed stock line 210 which merges into feed stockline 205. Valves 202*a* and 202*b* regulate into which of the vessels 23801 and 23803 the common (merged, feedline drains.

To allow the reaction to proceed at a lower pressure, the atmosphere above the reaction mixture is partially removed by closing the vents (not shown) on vacuum lines 221*a* and 221*b* and pulling a vacuum of about 0.1 bar abs, using an ethanol ring pump 215. The gases removed by the pump 215 are sent to the NaOH scrubber (not shown). Then the vacuum lines 221*a* and 221*b* are blocked by closing valves 216*a* and 216*b* and the contents of each of the vessels 23801 and 23803 are quickly heated to 105° C. utilizing steam on each of the vessel jackets (not shown) and resulting in a pressure increase to about 2.0–2.5 bar abs. Then the temperature is increased gradually from 105° C. to 115° C. over a six-hour period.

The reaction mixture is maintained at that temperature until a reduction of the chloropropyltriethoxysilane concentration below 2% is verified with analytical methods by analyzing samples taken from pipeline 218 through valve 219. This reaction usually takes about 8 to 10 hours.

After the reaction, the suspension is cooled down to about 25° C. by running cooling water through the jackets (not shown) of the vessels 23801 and 23803. This cooling step takes about 30 minutes. The resulting vacuum is then broken with nitrogen from supply line 203*a* and 203*b* having valves 204*a* and 204*b* and the suspension is emptied out of the vessels 23801 and 23803 through pipelines 223a and 223b having valves 217a and 217b, through a pipeline 218 and then through pipeline 226 having a valve 222 by using a centrifugal pump 214, through pipeline 224 having valve 225, and by pipeline 231 (shown in FIG. 11) into the distillation vessel 23839 (shown in FIG. 11).

Figure 11:
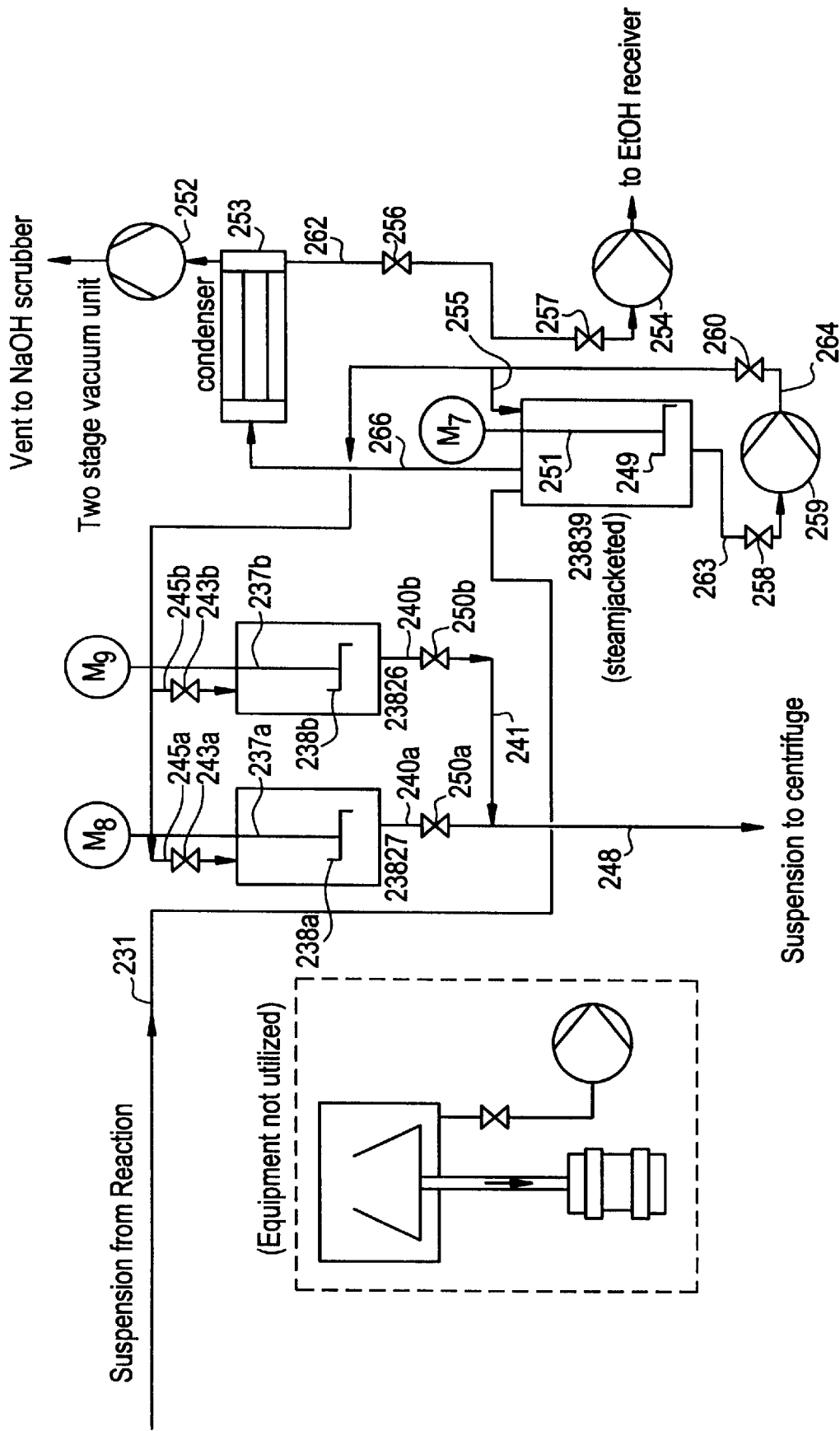
FIG. 11 is a schematic diagram of the second embodiment according to the invention wherein the distillation step of the invention follows the reaction step.

FIG. 11 illustrates in detail the distillation step shown in the flow diagram of FIG. 9. The distillation vessel 23839 which is equipped with a circulating means 251 having an agitator 249 and a motor $M_7$ for circulating the suspension, and a jacket (not shown). The suspension is boiled and the evaporated ethanol from the distillation vessel 23839 is transferred by conduit 266 and condensed in a chilled water-driven condenser 253, while maintaining a vacuum generated by a two-stage vacuum unit 252. Gases resulting from the vacuum unit are vented to the NaOH scrubber (not shown). The distillate is transferred by fall line 262 having valves 256 and 257 and pumped using pump 254 to the ethanol receiver 23857 (shown in FIG. 12), which supplies wash liquid to the centrifuge. Distillation takes significantly less time than the previously employed process due to the lower amount of ethanol to be evaporated. The ethanol concentration in the final product must be below 0.3%. Otherwise, the flashpoint of the material would be low enough to require packaging and transport as flammable liquid. After the ethanol concentration in the suspension is brought within specification, the suspension is cooled to about 7° C., utilizing chilled water on the jacket (not shown) of the distillation vessel 23839.

The cold suspension is then pumped from pipeline 263 having a valve 258, which couples the distillation pot 23839 and a pump 259 and is transferred by pipeline 264 having a valve 260 and stored in one of two parallel agitated holding vessels 23827 and 23826 which are connected to pipeline 264 by branch pipelines 245a and 245b having valves 243a and 243b. A recirculation line 255 is used to prevent solids from settling out of suspension during distillation. The vessels 23827 and 23826 are equipped with circulating means 237a and 237b having agitators 238a and 238b and motors $M_8$ and $M_9$. The suspension is transferred by pipelines 240a and 240b having valves 250a and 250b, which pipelines are connected by pipeline 241, which in turn is connected to pipeline 248, and then introduced into a manually operated filter centrifuge 270 (shown in FIG. 12).

Figure 12:
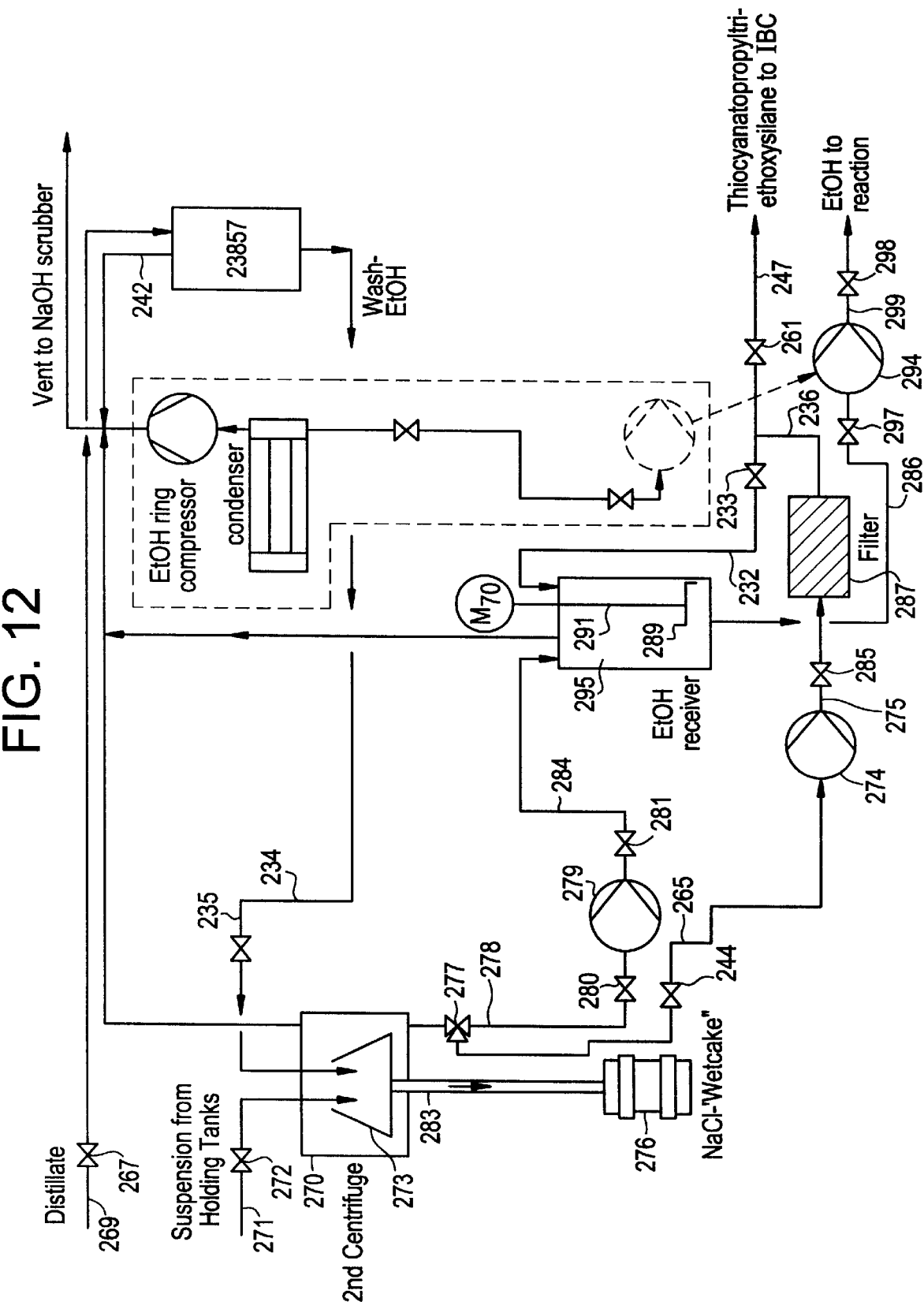
FIG. 12 is a schematic diagram of the second embodiment according to the invention wherein the centrifugation step follows the distillation step.

The centrifugation step in the flow diagram of FIG. 9 shown in detail in FIG. 12 and is conducted similarly to the previously employed process.

The suspension is introduced from holding vessels 23827 and 23826 (shown in FIG. 11) through pipeline 271 having a valve 272 into a filter centrifuge 270 provided with a basket 273. The difference between the process of the invention and the previously employed process is that the filtrate is routed via a three-way valve 277 and a filter unit 287 into the final packaging according to the invention as shown in FIG. 12.

After passing through the three-way valve 277, the thiocyanatopropyltriethoxysilane filtrate is discharged into pipeline 265 having a valve 244 and is pumped by a pump 274 to a filter unit 287 via a pipeline 275 having a valve 285. The filtrate is then transferred through a pipeline 236 to a branch pipeline 247 through valve 261 to an intermediate bulk container (IBC). Hereby, valve 233 in line 232 is closed.

Another difference between the invention and the previously employed process is that the ethanol distillate from the distillation step of FIG. 11 is transferred in a pipeline 269 having valve 267 to an ethanol receiver 23857. The distillate is transferred from the ethanol receiver 23857 through pipeline 234 having valve 235 to the centrifuge 270 and is used as wash ethanol to wash the filter cake of salt. Ethanol receiver 23857 is vented via conduit 242 to a NaOH scrubber (not shown).

Before a wash cycle, the centrifuge is allowed to spin dry and the three-way valve 277 is switched allowing the wash liquid to be discharged into pipeline 278 having a valve 280 and pumped by a pump 279 through a pipeline 284 having a valve 281 into the ethanol receiver 295, which holds ethanol that is used as a solvent in the reaction step. The ethanol receiver 295 is a holding vessel equipped with a circulating means 291 having an agitator 289 and a motor $M_{10}$. The ethanol is discharged through pipeline 286 having a valve 297 and pumped by a pump 294 to the reaction vessels 23801 and 23803 (shown in FIG. 10) via pipeline 299 having a valve 298. After the cake has spun to dryness, it is peeled and transferred by conduit 283 into grounded steel drums 276 using a hydraulic plow (not shown). To avoid contamination of successive filtrate with wash ethanol soaked in residual cake, it is necessary to remove as much cake as possible by manually scraping the filter cloth (not shown). This activity takes about 10 to 15 minutes and adds one hour per batch.

Example 4
Laboratory report regarding formation of bis (triethoxysilylpropyl)disulfane 3-thiocyanatopropyltriethoxysilane is produced by heating chloropropyltriethoxysilane with sodium thiocyanate in the presence of ethanol under elevated pressure as in the following reaction.

Past experience has shown that a higher reaction temperature causes a faster completion of the reaction as evidenced by the depletion of the chloropropyltriethoxysilane concentration below 2%. Higher temperatures also cause the generation of bis(triethoxysilylpropyl)disulfane, an indicator for the presence of unwanted side products that can cause discoloration of the particles above 0.3%. Bis (triethoxysilylpropyl)disulfane is thought to be generated according to the following and similar equation:

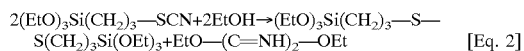

The previously employed process removed the precipitated salt before stripping off the ethanol. Also, the effluent of the wash phase in the centrifuge was mixed with the filtrate which increased distillation time in the previously employed process, which is summarized as follows:

Reaction→Solid Removal→Distillation→Solid Removal

In an effort to reduce both batch times and operating costs, several potential process improvements are identified with the most promising being the segregation of the wash liquid and the filtrate in the centrifuge according to the first embodiment of the invention and the reversal of process steps centrifugation and filtration as follows according to the second embodiment:

Reaction→Distillation→Solid Removal

Laboratory tests were conducted to assess the effect of these embodiments on the generation of the side product bis (triethoxysilylpropyl)disulfane, thus the generation of unwanted side products.

Apparatus

Reactor: 500 ml 316 SS LC series with cooling loop, sample port, magnetically coupled agitator, and electric mantle with self-adapting PID controller.

Distillation apparatus: 500 ml flat bottom three-neck flask on stirred hot plate, 300 mm Allihn type condenser driven with chilled water, 100 ml distillate receiver, water-driven ejector as a vacuum source.

Solid removal: 250 ml filtration flask under 56 mm Buchner funnel; Whatman #42 filter paper, water-driven ejector.

Gas chromograph: HP 5890 GC/TCD; Column: SPB-5, 0.53 mm*60 cm, 0.3 $\mu$m film; injector temp: 250° C.; Detector temp.: 60° C./3 min, 10° C./min, 315° C./10 min.

Procedure

1. Into reactor vessel, add 240 g (1 mol) chloropropyltriethoxysilane, 85 g (1.05 mol) NaSCN and 95 g (2 mol) EtOH.

2. Seal the reactor. Pull vacuum on reactor until pressure falls below −30 in. Hg. Cut off the vacuum.

3. Heat up the content of reactor to 140° C. and hold that temperature throughout the reaction.

4. Once the reactor has reached 140° C., pull a GC sample every hour to check the progress of the reaction.

5. Stop the reaction when either chloropropyltriethoxysilane concentration falls below 2% or bis(triethoxysilylpropyl)disulfane concentration goes above 0.3%.

6. Cool down the reactor using chilled water through cooling loop. Transfer the suspension into a heated and magnetically stirred three-neck flat-bottom flask.

7. Distill off ethanol under vacuum.

8. Filter the residue. Collect the filtrate for final GC analysis.

9. Wash the filter cake with ethanol from distillation. Save the wash ethanol for next batch trial.

The above procedure was repeated three times, always recycling the ethanol from the crystal wash as solvent ethanol in the reaction step. The reactor temperature was gradually increased from 110° C. in the first batch to 120° C. in the second batch to 140° C. in the third batch. In none of the batches, a generation of bis(triethoxysilylpropyl)disulfane forming concentrations above the detection limit could be observed. The calibration/sensibility of the GC has been verified several times by analyzing samples "spiked" with bis(triethoxysilylpropyl)disulfane standard.

Results

Four samples were extracted during the reaction of the third batch which took about 45 minutes to heat up to temperature and which was allowed to remain at temperature for about 3 hours. The analytical results calculated as "without ethanol" are shown below:

| Reaction Time (Hours) | Chloropropyltriethoxysilane % | Thiocyanatopropyltriethoxysilane % | Siloxane % | Bis (triethoxysilylpropyl)-disulfane % |
| --- | --- | --- | --- | --- |
| 0 | 65.7 | 13.5 | 1.0 | nd |
| 1 | 8.7 | 67.6 | 9.5 | nd |
| 2 | 3.7 | 73.9 | 10.8 | nd |
| 3 | .3 | 80.0 | 11.7 | nd |

Conclusion

This data shows no correlation between the process changes described above and the generation of bis(triethoxysilylpropyl)disulfane as an indicator of unwanted side products. The formation of excessive amounts of thiocyanatopropyltriethoxysilane dimer (Siloxane) in the third batch can be explained in part by the usually high reaction temperature.

Further variations and modifications of the foregoing will be apparent to those skilled in the art and are intended to be encompassed by the claims appended hereto.

I claim:

1. A process for manufacturing thiocyanatoalkyltrialkoxysilane comprising reacting a mixture of chloroalkyltrialkoxysilane and sodium thiocyanate in an alcohol to form a salt- and alcohol-containing thiocyanatoalkyltrialkoxysilane suspension;

centrifugating said suspension to separate salt resulting from said reacting step from an alcohol-containing thiocyanatoalkyltrialkoxysilane centrifugate;

washing said salt with alcohol;

adding the alcohol from the washing step to the mixture in the reacting step;

distilling said centrifugate to remove alcohol and to form a thiocyanatoalkyltrialkoxysilane residue; and removing solids from said thiocyanatoalkyltrialkoxysilane residue to form a thiocyanatoalkyltrialkoxysilane product.

2. The process for manufacturing thiocyanatoalkyltrialkoxysilane defined in claim 1 further comprising washing said salt separated in said centrifugating step with said alcohol from said distilling step.

3. The process for manufacturing thiocyanatoalkyltrialkoxysilane defined in claim 1 wherein said thiocyanatoalkyltrialkoxysilane is thiocyanatopropyltriethoxysilane, wherein said chloroalkyltrialkoxysilane is chloropropyltriethoxysilane, and wherein said alcohol is ethanol.

4. The process for manufacturing thiocyanatoalkyltrialkoxysilane defined in claim 2 wherein said thiocyanatoalkyltrialkoxysilane is thiocyanatopropyltriethoxysilane, wherein said chloroalkyltrialkoxysilane is chloropropyltriethoxysilane, and wherein said alcohol is ethanol.

5. A process for manufacturing thiocyanatoalkyltrialkoxysilane comprising distilling a thiocyanatoalkyltrialkoxysilane product suspension to form distilled alcohol and a thiocyanatoalkyltrialkoxysilane residue, wherein said product suspension is formed by reacting a mixture of chloroalkyltrialkoxysilane and sodium thiocyanate in alcohol, wherein salt generated by reacting said chloroalkyltrialkoxysilane and said sodium thiocyanate is removed from said suspension before said distilling step, wherein said salt is washed with said distilled alcohol, and adding alcohol used to wash said salt to said mixture.

6. The process for manufacturing thiocyanatoalkyltrialkoxysilane defined in claim 5 wherein said thiocyanatoalkyltrialkoxysilane is thiocyanatopropyltriethoxysilane, wherein said chloroalkyltrialkoxysilane is chloropropyltriethoxysilane, and wherein said alcohol is ethanol.

7. A process for manufacturing thiocyanatoalkyltrialkoxysilane by reacting a mixture of chloroalkyltrialkoxysilane and sodium thiocyanate in alcohol to form a salt- and alcohol-containing thiocyanatoalkyltrialkoxysilane suspension;

centrifugating said suspension to separate salt resulting from said reacting step from the alcohol-containing thiocyanatoalkyltrialkoxysilane centrifugate; and washing said salt with alcohol;

wherein an improvement comprises adding the alcohol from the washing step to the mixture in the reacting step; and distilling said alcohol-containing centrifugate to form distilled alcohol and a thiocyanatoalkyltrialkoxysilane residue.

8. The process for manufacturing thiocyanatoalkyltrialkoxysilane defined in claim 7, further comprising removing solids from said thiocyanatoalkyltrialkoxysilane residue to form a thiocyanatoalkyltrialkoxysilane product.

9. The process for manufacturing thiocyanatoalkyltrialkoxysilane defined in claim 7 wherein said thiocyanatoalkyltrialkoxysilane is thiocyanatopropyltriethoxysilane, and wherein said alcohol is ethanol.

10. The process for manufacturing thiocyanatoalkyltrialkoxysilane defined in claim 8 wherein said thiocyanatoalkyltrialkoxysilane is thiocyanatopropyltriethoxysilane, and wherein said alcohol is ethanol.

11. A process for manufacturing thiocyanatoalkyltrialkoxysilane comprising reacting a mixture of chloroalkyltrialkoxysilane and sodium thiocyanate in alcohol to form a thiocyanatoalkyltrialkoxysilane suspension;

distilling said suspension to form distilled alcohol and a thiocyanatoalkyltrialkoxysilane residue;

centrifugating said residue to separate salt resulting from said reacting step from a thiocyanatoalkyltrialkoxysilane centrifugate;

washing said salt with said distilled alcohol; and adding alcohol from the washing step to the mixture in the reacting step.

12. The process for manufacturing thiocyanatoalkyltrialkoxysilane defined in claim 11 wherein said thiocyanatoalkyltrialkoxysilane is thiocyanatopropyltriethoxysilane, and wherein said alcohol is ethanol.

13. A process for manufacturing thiocyanatoalkyltrialkoxysilane comprising distilling a thiocyanatoalkyltrialkoxysilane product suspension resulting from a reaction of a mixture of chloroalkyltrialkoxysilane and sodium thiocyanate in alcohol, to form distilled alcohol, and a thiocyanatoalkyltrialkoxysilane residue, and subsequently centrifugating said thiocyanatoalkyltrialkoxysilane residue to remove salt generated by reacting said chloroalkyltrialkoxysilane and said sodium thiocyanate.

14. The process for manufacturing thiocyanatoalkyltrialkoxysilane defined in claim 13, further comprising washing said salt with distilled alcohol; and adding alcohol used to wash said salt to said mixture.

15. The process for manufacturing thiocyanatoalkyltrialkoxysilane defined in claim 13 wherein said thiocyanatoalkyltrialkoxysilane is thiocyanatopropyltriethoxysilane, and wherein said alcohol is ethanol.

16. The process for manufacturing thiocyanatoalkyltrialkoxysilane defined in claim 14 wherein said thiocyanatoalkyltrialkoxysilane is thiocyanatopropyltriethoxysilane, and wherein said alcohol is ethanol.

\* \* \* \* \*